May 1, 1973 F. W. ANDERSON Plant Pat. 3,325
NECTARINE TREE
Filed Sept. 23, 1971
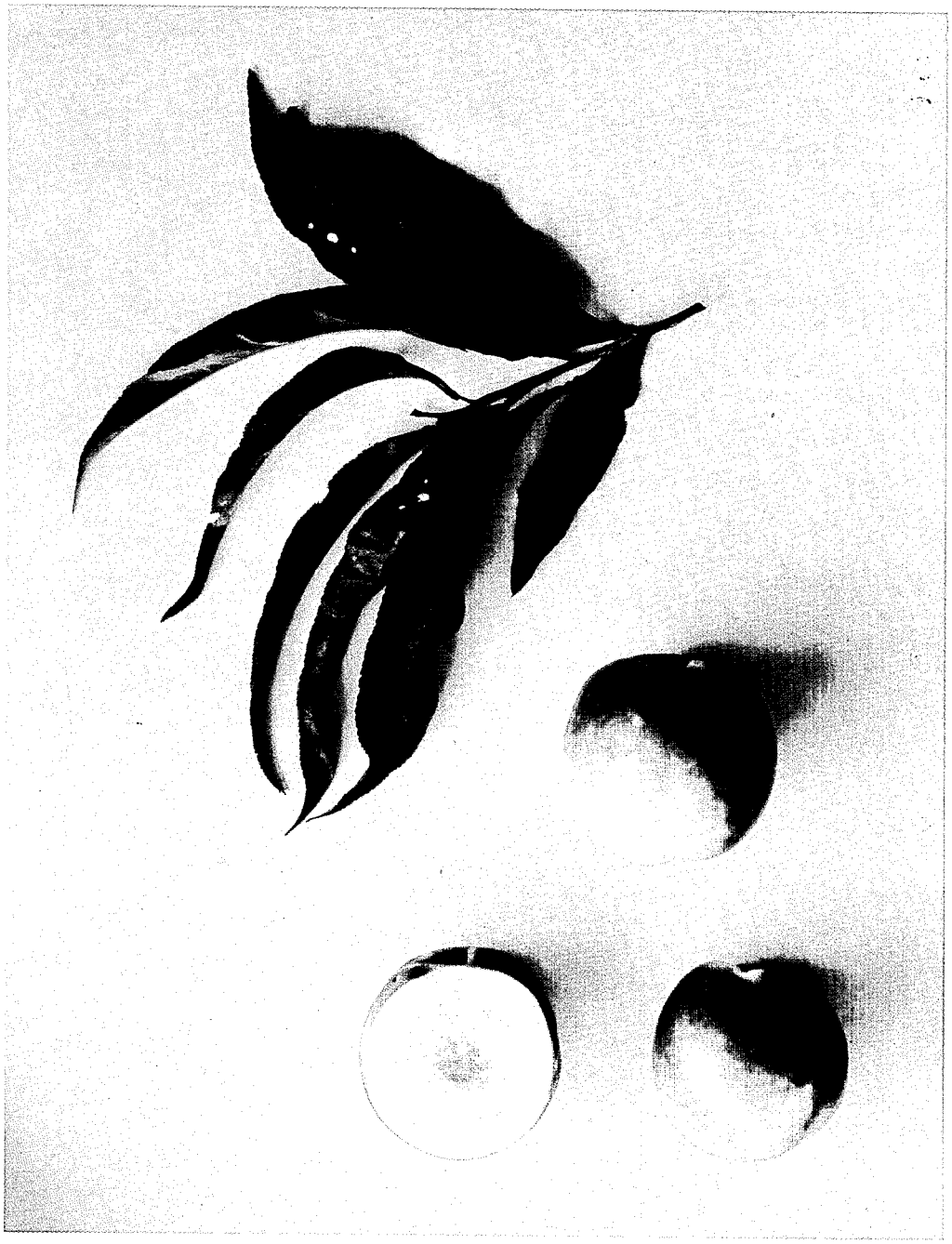

United States Patent Office

Plant Pat. 3,325
Patented May 1, 1973

3,325

NECTARINE TREE

Frederick W. Anderson, Merced, Calif., assignor to Reedley Nursery, Inc., Reedley, Calif.

Filed Sept. 23, 1971, Ser. No. 183,285
Int. Cl. A01h 5/03
U.S. Cl. Plt.—41 1 Claim

ABSTRACT OF THE DISCLOSURE

A dwarf nectarine tree which is of medium size, vigorous, spreading, dense, foliated with large acutely pointed lanceolate leaves having a crenate margin and reniform glands, and a regular and very productive bearer of medium to small size, uniform, symmetrical, globose, clingstone fruit—which ripens about a month before the freestone Golden Prolific (United States Plant Patent No. 2,193)—having yellow skin substantially overspread with red, and firm, crisp, yellow flesh; the surface of the pit cavity being red, and the flesh having flecks of red therein.

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The herein claimed new and distinct variety of nectarine tree was originated by me, in my experimental orchard located as aforesaid, as a selection from a block of open-pollinated seedlings which resulted from a planting of a large number of seeds of the Empress (United States Plant Patent No. 2,533) dwarf peach. Such seedlings—of which about three-fourths were peaches and the remainder nectarines—were maintained under careful and continuing observation, and—when they bore fruit—one of the seedling nectarines (and which is the present variety) evidenced commercially desirable characteristics. I, therefore, undertook asexual reproduction of such variety preparatory to introducing it to the trade.

ASEXUAL REPRODUCTION OF THE VARIETY

Subsequent to origination and selection by me of the present variety of nectarine tree, in the manner above described, I asexually reproduced it by top working on mature nectarine trees in my said experimental orchard, and in maturity such reproductions ran true to the original tree in all respects.

SUMMARY OF THE VARIETY

The herein claimed new and distinct, dwarf variety of nectarine tree is of medium size, vigorous, spreading, dense, foliated with large acutely pointed lanolate leaves having a crenate margin and reniform glands, and a regular and very productive bearer of medium to small size, uniform, symmetrical, globose, clingstone fruit having yellow skin substantially overspread with red, and firm, crisp, yellow flesh; the surface of the pit cavity being red, and the flesh having flecks of red therein.

The fruit of the present variety—which ripens about a month before the freestone Golden Prolific—is, by virtue of its firm flesh, of better long distance shipping quality, and which firmness also assures of an excellent shelf life.

BRIEF DESCRIPTION OF THE DRAWING

The drawing is an illustration, by photographic reproduction in color, of a twig with leaves, and detached fruit of the variety; one fruit having a portion cut away to expose the flesh.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Type.*—Dwarf.
- *Size.*—Medium.
- *Vigor.*—Vigorous.
- *Growth.*—Spreading.
- *Density.*—Dense.
- *Productivity.*—Very productive.
- *Bearing.*—Regular bearer.

Trunk:
- *Size.*—Stocky.
- *Texture.*—Shaggy.

Branches:
- *Size.*—Stocky.
- *Texture.*—Medium.

Leaves:
- *Size.*—Large; average length—7"; average width—1 13/16".
- *Form.*—Lanceolate; acutely pointed.
- *Texture.*—Smooth.
- *Margin.*—Crenate.
- *Petiole.*—Medium to short.
- *Glands.*—Number and position—usually 2 or 3 on blade and 2 on petiole; alternate; medium size; reniform.
- *Color.*—Top side—Medium green (23–H–9); under side—Lighter green (22–H–8).

Flowers:
- *Blooming period.*—Medium as compared with other varieties. March 5–14, 1970.
- *Size.*—Large.

Fruit:
- *Maturity when described.*—Eating ripe.
- *Date of first picking.*—July 17, 1970.
- *Date of last picking.*—July 27, 1970.
- *Size.*—Uniform; medium to small; average diameter axially—2⅛"; average transversely in suture plane—2⅛".
- *Form.*—Uniform; symmetrical; globose.
- *Suture.*—Distinct; shallow; extends from base to beyond apex; marked depression beyond pistil point.
- *Base.*—Truncate.
- *Apex.*—Short; depressed.

Skin:
- *Thickness.*—Medium.
- *Tendency to crack.*—None.
- *Down.*—Wanting.
- *Color.*—Yellow (10–L–6) substantially overspread with red (6–L–5) shading slightly darker on sunny side; there being considerable sheen.

Flesh:
- *Texture.*—Firm; crisp.
- *Ripens.*—Evenly.
- *Flavor.*—Subacid; mild.
- *Eating quality.*—Fair to good.
- *Color.*—Yellow (11–L–6), with red (5–L–3) pit cavity; there being red flecks in the flesh.

Stone:
- *Type.*—Cling.

*Size.*—Medium; average length — 1⅛"; average breadth—1 1/16"; average thickness—¾".

*Tendency to split.*—Slight.

*Color.*—Garnet red (7–H–6).

Use: Market—local and long distance shipping.

Resistance to insects and diseases: No unusual susceptibilities noted.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of dwarf nectarine tree, substantially as shown and described, which is of medium size, vigorous, spreading, dense, foliated with large acutely pointed lanceolate leaves having a crenate margin and reniform glands, and a regular and very productive bearer of medium to small size, uniform, symmetrical, globose, clingstone fruit—which ripens about a month before the freestone Golden Prolific—having yellow skin substantially overspread with red, and firm, crisp, yellow flesh; the surface of the pit cavity being red, and the flesh having flecks of red therein.

No references cited.

ROBERT E. BAGWILL, Primary Examiner